(12) United States Patent
Hosoi et al.

(10) Patent No.: US 6,255,048 B1
(45) Date of Patent: Jul. 3, 2001

(54) HIGHLY SENSITIVE FLUOROASSAY

(75) Inventors: Shigeru Hosoi, Hamakita; Makiko Kojima, Matsumoto; Sachiko Kadouchi, Hamakita, all of (JP)

(73) Assignee: Laboratory of Molecular Biophotonics, Shizuoka (JP)

( * ) Notice: Subject to any disclaimer, the term of this patent is extended or adjusted under 35 U.S.C. 154(b) by 0 days.

(21) Appl. No.: 09/011,223

(22) PCT Filed: Jun. 9, 1997

(86) PCT No.: PCT/JP97/01960

§ 371 Date: Feb. 9, 1998

§ 102(e) Date: Feb. 9, 1998

(87) PCT Pub. No.: WO97/47968

PCT Pub. Date: Dec. 18, 1997

(30) Foreign Application Priority Data

Jun. 10, 1996 (JP) .................................................. 8-170637

(51) Int. Cl.[7] ............ C12Q 1/68; G01N 33/53; G01N 33/574; G01W 33/543
(52) U.S. Cl. ............ 435/6; 435/7.1; 435/7.23; 435/7.24; 435/7.95; 436/518; 436/964; 436/828
(58) Field of Search .................. 435/6, 7, 7.23, 435/7.24, 7.95; 436/518, 964, 828

(56) References Cited

U.S. PATENT DOCUMENTS 4,921,788  5/1990  Deutsch .

FOREIGN PATENT DOCUMENTS

| 2196998 | 5/1997 | (CA) . | |
|---|---|---|---|
| 131830 | * 1/1985 | (EP) | ............ C12Q/1/68 |
| 0154884 | * 9/1985 | (EP) . | |
| WO91/17442 | 11/1991 | (EP) . | |
| WO94/26932 | 11/1994 | (EP) . | |
| 0 698792 A1 | 2/1996 | (EP) . | |
| 60-226900 | 11/1985 | (JP) . | |
| 2-51063 | 2/1990 | (JP) . | |
| 7-265076 | 10/1995 | (JP) . | |

OTHER PUBLICATIONS

"Fluoroimmunoassays and Immunofluorometric Assays", Iikka Hemmila, Clinical Chemistry, vol. 31, No. 3, 1985.

"Rapid detection and counting of single bacteria in a wide field using a photon–counting TV camera", M. Masuko, S. Hosoi and T. Hayakawa, FEMS Microbiology Letters 83 (1991) 231–238.

"A novel method for detection and counting of single bacteria in a wide field using an ultra–high–sensitivity TV camera without a microscope", M. Masuko, S. Hosoi & T. Hayakawa, FEMS Microbiology Letters 81 (1991) 287–290.

* cited by examiner

Primary Examiner—Nita Minnifield
Assistant Examiner—Padma Baskar
(74) Attorney, Agent, or Firm—Pillsbury Winthrop LLP

(57) ABSTRACT

This invention provides fluoroassay which comprises labeling analyte molecules with a fluorescent material having a nucleic acid portion stained with a sufficient number of fluorochrome molecules so as to be measurable as fluorescent spots, and a reactive group binding to the analyte molecule specifically, immobilizing the labeled analyte on a solid phase, and counting the number of fluorescent spots. The nucleic acid portion of the fluorescent labeling material is a double-stranded or single-stranded nucleic acid, and the staining with the fluorochrome molecules is performed with intercalating type, minor groove binding type, or covalently binding to the nucleic acid type.

4 Claims, 11 Drawing Sheets

DOUBLE-STRANDED NUCLEIC ACID, INTERCALATING FLUOROCHROME(☆)

SPECIFICALLY BINDING REACTIVE GROUP

DOUBLE-STRANDED NUCLEIC ACID, MINOR GROOVE BINDING FLUOROCHROME(∼☆)

SINGLE-STRANDED NUCLEIC ACID,
COVALENT BONDING FLUOROCHROME(—☆)

DOUBLE-STRANDED NUCLEIC ACID,
COVALENT BONDING FLUOROCHROME(—☆)

50 μm

50 μm

50 μm

50 μm

50 μm

PGE2-BSA conc. (mg/ml)

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 18
      (B) TYPE: Nucleic acid
      (C) STRANDEDNESS: Single-stranded
      (D) TOPOLOGY: Linear (ii) MOLECULE TYPE: DNA (xi) SEQUENCE DESCRIPTION: SEQ ID NO: 1:

ATA CCG TCG ACC TCG AGG                18

(2) INFORMATION FOR SEQ ID NO: 2:

(i) SEQUENCE CHARACTERISTICS:
      (A) LENGTH: 18
      (B) TYPE: Nucleic acid
      (C) STRANDEDNESS: Single-stranded
      (D) TOPOLOGY: Linear (ii) MOLECULE TYPE: DNA (xi) SEQUENCE DESCRIPTION: SEQ ID NO: 2:

TCA CAC AGG AAA CAG CTA                18

(2) INFORMATION FOR SEQ ID NO: 3

(i) SEQUENCE CHARACTERISTICS:
      (A) LENGTH: 18
      (B) TYPE: Nucleic acid
      (C) STRANDEDNESS: Single-stranded
      (D) TOPOLOGY: Linear -continued

```
    (ii) MOLECULE TYPE: DNA (xi) SEQUENCE DESCRIPTION: SEQ ID NO: 3:

CGT CGA TTT TTG TGA TGC                                             18

(2) INFORMATION FOR SEQ ID NO: 4:

(i) SEQUENCE CHARACGTERISTICS:
        (A) LENGTH: 30
        (B) TYPE: Nucleic acid
        (C) STRANDEDNESS: Single-stranded
        (D) TOPOLOGY: Linear (ii) MOLECULE TYPE: DNA (xi) SEQUENCE DESCRIPTION: SEQ ID NO: 4:

TCG GTT GAA TGT CGC CCT TTT GTC TTT AGC                             30

(2) INFORMATION FOR SEQ ID NO: 5:

(i) SEQUENCE CHARACTERISTICS:
        (A) LENGTH: 33
        (B) TYPE: Nucleic acid
        (C) STRANDEDNESS: Single-stranded
        (D) TOPOLOGY: Linear (ii) MOLECULE TYPE: DNA (xi) SEQUENCE DESCRIPTION: SEQ ID NO: 5:

ATC ATT ATT TGA TTT CAA TTT TGT CCC ACT CCC                         33

(2) INFORMATION FOR SEQ ID NO: 6:

(i) SEQUENCE CHARACGTERISTICS:
        (A) LENGTH: 36
        (B) TYPE: Nucleic acid
        (C) STRANDEDNESS: Single-stranded
        (D) TOPOLOGY: Linear (ii) MOLECULE TYPE: DNA (xi) SEQUENCE DESCRIPTION: SEQ ID NO: 6:

AGG TCG CCG CCC CGT AAC CTG TCG GAT CAC CGG AAA                     36

(2) INFORMATION FOR SEQ ID NO: 7:

(i) SEQUENCE CHARACTERISTICS:
        (A) LENGTH: 30
        (B) TYPE: Nucleic acid
        (C) STRANDEDNESS: Double-stranded
        (D) TOPOLOGY: Linear (ii) MOLECULE TYPE: DNA (xi) SEQUENCE DESCRIPTION: SEQ ID NO: 7:

GAA CAA AGA AAC CAC CAG AAG GAG CGG AAT                             30
```

HIGHLY SENSITIVE FLUOROASSAY

This application is the national phase of international application PCT/ JP97/01960 filed Jun. 9, 1997 which designated the U.S.

TECHNICAL FIELD

The present invention relates to high sensitivity fluoroassay.

BACKGROUND ART

Many methods are known for detecting biological trace components, which are highly sensitive and specific. Briefly, in those methods a targeted trace analyte is detected or quantitatively determined by labeling the analyte with a suitable labeling material, immobilizing the labeled analyte on a suitable medium based on a specific binding reaction, thoroughly washing it, and then detecting the labeling material by suitable means. Examples of the specific binding reactions generally used are the antigen-antibody reaction, the avidin-biotin binding reaction, and the receptor-ligand binding reaction.

Labeling materials and methods for label detection are known to be of various types depending on the chemical and physical properties of the labeling materials. Usually, such methods are as follows: (1) The sum of signals, e.g., radiation doses, amounts of fluorescence, or amounts of luminescence (chemiluminescence, bioluminescence), from the trace analyte labeled with a labeling material and immobilized on a suitable solid phase is measured, and presence of the trace analyte is evaluated, and quantitatively determined, based on the correlation between measured values and concentrations of the trace analyte. (2) The number of the labeled analyte molecules immobilized on a suitable solid phase is counted by observing phenomena such as radiation, fluorescence, or luminescence (chemiluminescence, bioluminescence) from the labeling material, and presence of the trace analyte is evaluated, and quantitatively determined, based on the count. Method (2) requires that the trace labeled analytes immobilized on the solid phase are counted molecule by molecule. Compared with method (1), method (2) may have advantages, such as lower background noise, shorter measuring time, and decreased measurement errors (increased measurement sensitivity).

Thus, it is desirable to develop a method which comprises counting, individually, trace labeled analytes fixed to a suitable solid phase, based on presence or absence of signals from the labeling material, in order to evaluate the presence of the analyte and quantitatively determine the analyte.

The usual, known method of labeling an analyte with a fluorescent molecule should give single molecule detection under idealized conditions. However, it is difficult to use this method for the above-mentioned ultrahigh sensitivity detection under practical measuring conditions, which involves use of an ordinary fluorescence microscope. The amount of fluorescence emitted from a single fluorophore is usually very small partly because of rapid bleaching of the fluorochrome. That is, such signals from the labeled analyte are very small and weak. Since background fluorescence is also comparable with signal fluorescence, measurement of individual luminescence phenomena is virtually unpractical.

DISCLOSURE OF THE INVENTION

High sensitivity fluoroimmunoassay related to the present invention circumvents the above-described difficulties, and makes it possible to detect a fluorescent-labeled analyte with higher sensitivity. The first objective of the invention is to provide a fluoroimmunoassay which comprises the step of labeling an analyte with a labeling fluorescent material having a nucleic acid portion stained with multiple fluorochromes by an ordinary detecting means, and a specifically binding reactive group specifically binding to the analyte, and the step of detecting the fluorescence of the labeling fluorescent material.

The second objective of the invention is to provide the above-mentioned fluoroimmunoassay which further includes the step of immobilizing the labeled analyte on a solid phase.

Still another objective of the invention is to provide the above-mentioned fluoroimmunoassay wherein the step of detecting the fluorescence further uses optically magnifying means.

A further objective of the invention is to provide the above-mentioned fluoroimmunoassay wherein the optically magnifying means is a fluorescence microscope.

A still further objective of the invention is to provide the above-mentioned fluoroimmunoassay wherein the fluorescence of the labeling fluorescent material is counted as fluorescent spots in the microscope images obtained.

Further, an objective of the invention is to provide fluoroimmunoassay which comprises the step of labeling an analyte with a labeling fluorescent material, or probe, having a nucleic acid portion stained with fluorochromes, and a specifically binding reactive group specifically binding to the analyte, and the step of detecting the fluorescence of the labeling fluorescent material.

Another objective of the invention is to provide the fluoroimmunoassay which further includes the step of immobilizing the labeled analyte on a solid phase.

Still another objective of the invention is to provide the fluoroimmunoassay wherein the step of the fluorescence detection further uses optically enlarging means.

A further objective of the invention is to provide the fluoroimmunoassay wherein the optically enlarging means is a fluorescence microscope.

A still further objective of the invention is to provide the fluoroimmunoassay wherein the fluorescence of the labeling fluorescent material is counted as fluorescent spots in the microscope images obtained.

An additional objective of the invention is to provide the fluoroimmunoassay wherein the nucleic acid portion is a double-stranded nucleic acid having 100 to 50,000 bases, and the staining with the fluorochromes is performed with intercalating fluorochromes whose number is estimated to be 10 to 25% of the number of the bases.

A further additional objective of the invention is to provide the fluoroimmunoassay wherein the nucleic acid portion is a double-stranded nucleic acid having 1,000 to 5,000 bases, and the staining with the fluorochromes is performed with 100 to 1,200 intercalating fluorochromes.

A further additional objective of the invention is to provide the fluoroimmunoassay wherein the nucleic acid portion is a double-stranded nucleic acid having 100 to 50,000 bases, and the staining with the fluorochromes is performed by the fluorochromes binding to the minor groove of the double-helix, the number of the fluorochrome being 10 to 25% of the number of the bases.

A further additional objective of the invention is to provide the fluoroimmunoassay described above, wherein the nucleic acid portion is a single-stranded nucleic acid having 100 to 50,000 bases, and the staining with the fluorochromes, whose number is 10 to 70% of the number of the bases, is by covalently binding to the nucleic acid.

A further additional objective of the invention is to provide the fluoroimmunoassay wherein the nucleic acid portion is a double-stranded nucleic acid having 100 to 50,000 bases, and the staining with the fluorochromes, whose number is 10 to 70% of the number of the bases, is by covalently binding to the nucleic acid.

A further additional objective of the invention is to provide the fluoroimmunoassay wherein the specifically binding reactive group is biotin bound to a terminal of the nucleic acid.

A further additional objective of the invention is to provide the fluoroimmunoassay wherein the magnification of the fluorescence microscope is 20× to 100× magnification at the objective.

BEST MODE FOR CARRYING OUT THE INVENTION

The present invention is concerned with labeling materials for high sensitivity fluorescence detection As schematically shown in FIGS. 1A through 1D, the labeling material for high sensitivity fluorescence detection of the present invention is (1) a double-stranded or single-stranded nucleic acid labeled with fluorochromes giving fluorescence intensity high enough to be counted molecule by molecule under an ordinary fluorescence microscope, and (2) a labeling material having a specifically binding reactive group for labeling. To give fluorescent spots of such intensity in a micrograph, the labeling material for high sensitivity fluorescence detection of the invention is a labeling molecule of an adequate size to contain a sufficient number of fluorochromes therein.

Intercalating Fluorochrome-Stained Double-Stranded Nucleic Acid

Figure 1A:
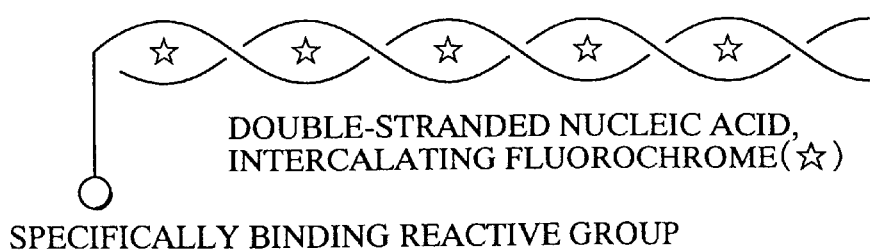
FIG. 1A shows an example of a multi-fluorochrome-stained labeling nucleic acid related to the present invention, wherein a labeling material comprising a double-stranded nucleic acid is stained with multiple intercalating fluorochromes.

A preferred embodiment of the labeling material relevant to the invention, as shown in FIG. 1A, is a double-stranded nucleic acid with a suitable number of bases, which can be stained with intercalating fluorochromes and which has a specifically binding reactive group. Since such a double-stranded nucleic acid has a sufficient number of bases, it is stained with the sufficient number of intercalating fluorochromes for molecular counting. An analyte labeled with this labeling material via the specifically binding reactive group generates sufficient fluorescence, and gives fluorescent spots which are observable individually under a fluorescence microscope. The number of bases and the type of the bases of the double-stranded nucleic acid are not restricted. However, the double-stranded nucleic acid is preferably a nucleic acid comprising 100 to 50,000 (more preferably 100 to 5,000) bases. If the number of bases is smaller than this range, it cannot give sufficient fluorescence for molecular counting. Thus, the analyte labeled with the resulting labeling material cannot give fluorescent spots of a size sufficient to be observed individually under a fluorescence microscope with an ordinary magnification (a 20X to 100X objective lense). If the number of bases of the nucleic acid is larger than the above range, the stability of the nucleic acid itself deteriorates, posing problems such as fragmentation. Thus, its handling becomes laborious, and its storage stability is diminished. In the case of an ordinary nucleic acid (DNA), intercalating fluorochromes can be stably incorporated into the nucleic acid upto about 25% of the number of bases of the nucleic acid. So a nucleic acid of 4,000 bases long, for example, can be stained with about 200 to 1,000 fluorochromes. Labeling with this large amount of fluorochromes provides fluorescent spots to be sufficiently recognized molecule by molecule with an ordinary fluorescence microscope.

To prepare a double-stranded nucleic acid of the required length, various known methods can be used. Preferred examples are a method based on chemical synthesis, a method based on enzymatic reaction, preparation from a naturally occurring nucleic acid, preparation by PCR or the like, and cloning with plasmid or phage.

The preparation method preferred in the present invention, as will be described later on, further requires that the nucleic acid be provided with a group having specific binding reactivity, and that the nucleic acid be prepared efficiently with a desired length. To fulfill both of these requirements, polymerase chain reaction (PCR) can preferably be used. As indicated in the Examples, the use of this method makes it easy to prepare a labeling probe of about 3,000 base length with biotin bound to a terminal of a nucleic acid strand.

The double-stranded probe of the invention is not limited in the type of the constituent nucleic acid. To prepare a double-stranded nucleic acid of the required length, therefore, various known methods can be used. Examples include a method based on chemical synthesis, a method based on enzymatic reaction, preparation from a naturally occurring nucleic acid, preparation by PCR or the like, and cloning with plasmid or phage.

There are no limitations on the intercalating dyes used as the fluorochromes for the double-stranded labeling material relevant to the invention so long as they give specific binding and bright-enough fluorescence. Preferred examples of the dyes are phenanthridinium intercalators such as ethidium bromide and propidium iodide, aminoactinomycin-D (7-AAD), 9-amino-6-chloro-2-methoxyacridine (ACMA), benzoxazolium-4-pyridinium (PO), benzothiazolium-4-pyridinium (BO), benzoxazolium-4-quinolinium (YO), and benzothiazolium-4-quinolinium (TO). Their dimers, POPO, BOBO, YOYO and TOTO, can also be used preferably. These dyes are known to perform intercalation such that one dye molecule is intercalated every several base pairs. Thus, a very large number of fluorochromes can be used for staining.

The above-described intercalating dyes preferably used in the invention are intercalated into a double helix to generate fluorescence. This type of dye can markedly decrease background fluorescence from the free dye remaining at the time of measurement.

The specifically binding reactive group of the probe of the invention depends on the specific reaction to be used. Examples of prefered reactions include antigen-antibody reaction, avidin-biotin binding reaction, and receptor-ligand binding reaction.

The way of linking the reactive group to the probe of the invention is not limited, and an ordinary organic synthesis reaction can be used. In the Examples to be described hereafter, a terminally biotinylated short nucleic acid can be used as a starting material, and the probe can be prepared by PCR.

Minor Groove Binding Fluorochrome-Stained Double-Stranded Nucleic Acid

Figure 1B:
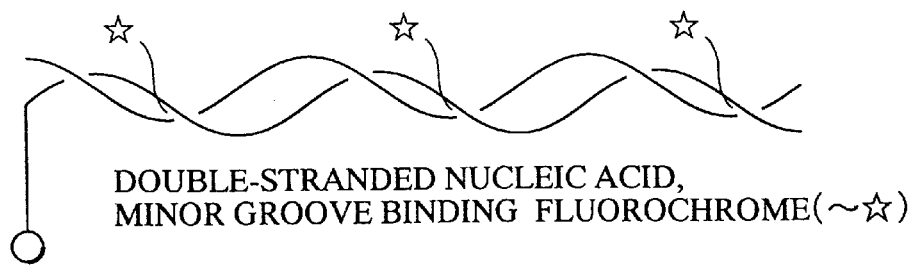
FIG. 1B shows an example of a fluorochrome-stained labeling nucleic acid related to the present invention, wherein a labeling material comprising a double-stranded nucleic acid contains minor groove binding fluorochromes covalent-bonded to the nucleotide.

Another preferred embodiment of the labeling material relevant to the invention, as shown in FIG. 1B, is a double-stranded nucleic acid with a suitable number of base sequences. This labeling material has basically the same double-stranded nucleic acid structure as in the intercalating fluorochrome-stained double-stranded nucleic acid explained in FIG. 1A, except that the double-stranded nucleic acid is stained with minor groove binding fluorochromes. The labeling material also has a specifically binding reactive group. Such a double-stranded nucleic acid has a sufficient number of bases, and is stained with the desired number of minor groove binding fluorochromes. An analyte labeled with this labeling material via the specifically binding reactive group generates sufficient fluorescence for molecular counting, and can give fluorescent spots which are observable individually under a fluorescence microscope. The number and the type of bases of the double-stranded nucleic acid are not restricted. Preferably, however, the double-stranded nucleic acid is a nucleic acid having a length of 100 to 50,000 (more preferably 100 to 5,000) base pairs. If the number of bases is smaller than this range, it cannot be stained with a sufficient number of minor group binding fluorochromes. Thus, the analyte labeled with the resulting labeling material cannot give fluorescent spots of a size sufficient to be observed molecule by molecule under a fluorescence microscope of an ordinary magnification (with a 20× to 100× objective lense). If the number of bases of the nucleic acid is larger than the above range, the nucleic acid itself becomes unstable, and poses problems such as fragmentation. Thus, its handling becomes laborious, and its storage stability is deteriorated. In the case of an ordinary nucleic acid (DNA), a sufficient number of minor groove binding fluorochromes can be incorporated into the nucleic acid, and fluorescent spots can be sufficiently recognized molecule by molecule with an ordinary fluorescence microscope.

To prepare a double-stranded nucleic acid of the required length, various known methods can be used. Preferred examples are a method based on chemical synthesis, a method based on enzymatic reaction, preparation from a naturally occurring nucleic acid, preparation by PCR or the like, and cloning with a plasmid or a phage.

The preparation method preferred in the invention, as will be described below, further requires that the nucleic acid be provided with a group having specific binding reactivity, and that the nucleic acid be prepared efficiently with a sufficient length. To fulfill both of these requirements, polymerase chain reaction (PCR) is preferably used. As shown in the Examples, the use of this method makes it possible to prepare a probe of about 3,000 base pairs having biotin linked to a terminal of a nucleic acid strand.

The double-stranded probe of the invention is not restricted by the type of the constituent nucleic acid. To prepare a double-stranded nucleic acid of the required length, therefore, various known methods can be used. Examples are a method based on chemical synthesis, a method based on enzymatic reaction, preparation from a naturally occurring nucleic acid, preparation by PCR or the like, and cloning with a plasmid or a phage.

As will be described below, the invention further requires that the nucleic acid be provided with a group having specific binding reactivity, and that the nucleic acid be prepared efficiently with a sufficient length. To fulfill both requirements, PCR is preferably used. As shown in the Examples, the use of this method makes it possible to prepare a probe having the length of about 3,000 base pairs with biotin linked to a terminal of a nucleic acid strand.

Examples of the minor groove binding dyes as the fluorochromes for the double-stranded labeling material relevant to the invention are Hoechst 33258 and 33342 (Hoechst AG), DAPI and DIPI.

The specifically binding reactive group of this type of labeling material, like the aforementioned intercalating labeling materials, depends on the specific reaction to be used. Examples of the prefered reaction are antigen-antibody reaction, avidin-biotin binding reaction, and receptor-ligand binding reaction.

The way of linking the reactive group to the probe of the invention is not limited, and an ordinary organic synthesis reaction can be used. In the Examples to be described below, a terminally biotinylated short nucleic acid is used as a starting material, and the probe is prepared by PCR.

Single-Stranded Nucleic Acid with Covalently Bound Fluorophores

Figure 1C:
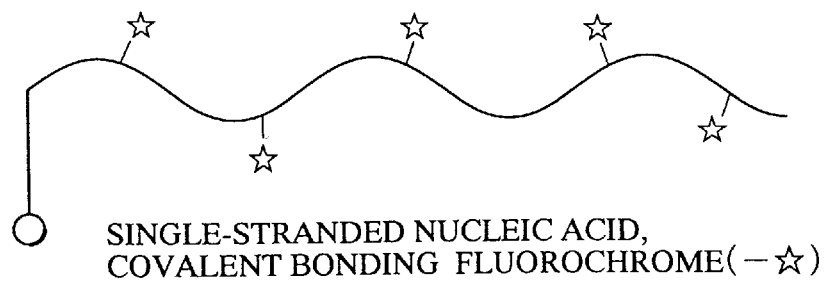
FIG. 1C shows an example of a multi-fluorochrome-stained labeling nucleic acid related to the present invention, wherein a labeling material comprising a single-stranded nucleic acid contains fluorochromes covalently bonded to nucleotides.

Still another preferred embodiment of the labeling material relevant to the invention, as shown in FIG. 1C, is single-stranded nucleic acid with a suitable number of bases, with fluorochromes linked to the nucleic acid via chemical bonds. This nucleic acid of the single-stranded structure is not limited in the number or the type of the constituent bases, as long as it can be labeled with a sufficient number of fluorochromes to be described.

As is explained below, labeling needs to be performed with a sufficient number of fluorochromes in order to make one labeled analyte molecule to be detectable. For this purpose, it is preferred that the nucleic acid be long enough for the purpose. To handle the probe of the invention stably and simply under ordinary operating conditions and storage conditions, too long a nucleic acid is liable to degradation and is inconvenient to handle. Thus, the probe of the invention is preferably a single-stranded nucleic acid comprising 100 to 50,000 bases, more preferably, 100 to 5,000 bases. When this probe is prepared by polymerase chain reaction using a fluorochrome-labeled nucleotide to be described, for example, it can be labeled with fluorochromes in a number corresponding to about 25% of the number of bases of the nucleic acid. A nucleic acid 4,000 bases long, for example, can usually be stained with about 200 to 1,000 fluorochromes. Labeling with this fluorochrome-incorporated probe enables fluorescent spots to be sufficiently recognized molecule by molecule with an ordinary fluorescence microscope.

The single-stranded probe of the invention is not limited in the type of the constituent nucleic acid. To prepare a single-stranded nucleic acid of the required length, various known methods can be used. Examples are a method based on chemical synthesis, a method based on enzymatic reaction, preparation from a naturally occurring nucleic acid, preparation by PCR or the like, and cloning with a plasmid or a phage.

The present invention, as will be described, further requires that a group having specific binding reactivity be linked to the nucleic acid, and that the nucleic acid be prepared efficiently with a sufficient length. To fulfill both requirements, it is preferred to perform PCR using a fluorochrome-labeled nucleotide. The product may be obtained as single strands by a suitable treatment. As shown in the Examples, the use of this method makes it easy to prepare a probe of up to about 3,000 base length with biotin linked to a terminal of a nucleic acid strand.

The fluorochrome labeling reaction for the above single-stranded labeling material is not limited. A nucleotide having fluorochromes linked thereto via various covalent bonding may be incorporated into the labeling material by various known synthetic methods. For example, an oligonucleotide or a single-stranded DNA can be labeled with single-strand specific dyes such as OliGreen(TM) (Molecular Probe). In this case, a considerable number, with respect to the number of the bases of the nucleic acid, of fluorochromes can be linked so that the nucleic acid molecules can be visualized. Labeling with a so prepared fluorochrome-stained probe permits fluorescent spots to be recognized molecule by molecule efficiently with an ordinary fluorescence microscope.

This staining via covalent bonding is highly stable under ordinary washing conditions, and can further reduce the background fluorescence compared with non-covalent staining methods.

The specifically binding reactive group depends on the specific reaction to be used, as in the aforementioned intercalating probes. Examples of prefered reactions include antigen-antibody reaction, avidin-biotin binding reaction, and receptor-ligand binding reaction.

The way of linking the reactive group to the probe of the invention is not limited, and an ordinary organic synthesis reaction can be used. In the Examples to be described, a terminally biotinylated short nucleic acid is used as a starting material, and the probe is prepared by PCR.

Double-Stranded Nucleic Acid with Covalently Bound Fluorochromes

Figure 1D:
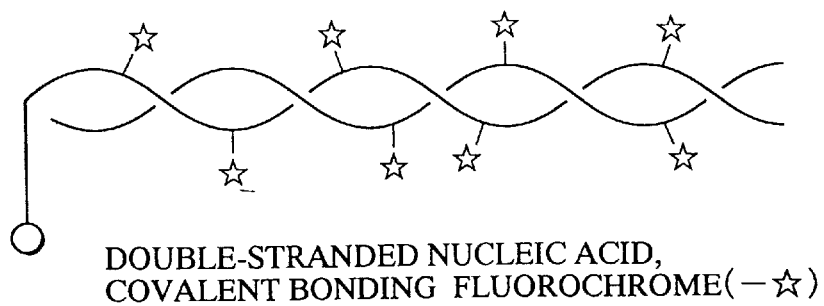
FIG. 1D shows an example of a multi-fluorochrome-stained labeling nucleic acid related to the present invention, wherein a labeling material comprising a double-stranded nucleic acid contains fluorochromes covalently bonded to nucleotides.

A further preferred embodiment of the labeling material relevant to the invention, as shown in FIG. 1D, is the double-stranded form with fluorophores attached covalently. This labeling material can have twice as many fluorochromes as those of the aforementioned single-stranded nucleic acid.

Method of High Sensitivity Fluorescence Detection

The detecting method of the invention relies on measuring the fluorescence of an analyte labeled with the labeling fluorescent material of the invention described above. The fluorescence of the labeled analyte can be detected by the following methods: (1) total fluorescence intensities from a restricted area are measured; and (2) individual fluorescence from the respective labeled analyte molecule are detected and counted as spots after immobilization means and magnification.

Method (1) for measuring total fluorescence intensities can be performed by measuring a solution containing a labeled analyte or a solid phase (e.g., microtiter plate, glass slide, or membrane) adsorbing the labeled analyte by means of fluorescence measuring means usually known to the public. One example of the measuring means is a microtiter plate reader. The optical detector suitable for this purpose is, for instance, I-CCD(intensified charge coupled device), SIT (silicone intensified target camera), PMT(photo-multiplier tube) or APD(avalanche photosiode). Fluorescence intensity obtained can be processed by a data analyzing method usually known to the public. For example, a standard curve of concentration vs. total fluorescence intensities is obtained using standard samples of known concentrations, whereby the analyte of an unknown concentration can be determined.

According to the invention, it is also possible to carry out Method (2) in which the labeled analyte is immobilized on a suitable solid phase, and if desired, labeled analyte molecules are counted as spots by suitable enlarging means. The method of the invention is not limited to the immobilized analyte, as long as the method is performed within the time required for counting the fluorescent spots and the fluorescent spots are not substantially drifted. For example, the method of measurement in a highly viscous medium such as glycerin is feasible. It is also permissible to immobilize the labeled analyte on a suitable solid phase by a suitable treatment. Examples of the solid phase for immobilization that can be used preferably in the invention are microplate, slide glass, and various membranes. Desirably, the solid phase itself should be a low fluorescence or a non-fluorescence one. The method for immobilization in the invention is not limited, and may use chemical bonding usually known to the public, or protein-protein specific binding reaction.

The method of using chemical bonding comprises introducing a reactive group (e.g., a hydroxyl group) onto the solid phase by a suitable treatment, and further introducing into the group a binding group which specifically reacts with the analyte. If desired, a suitable linker portion may further be used as a mediator. The method of using a protein-protein specific binding reaction may be any of the various known immunoassay methods without limitation imposed thereon.

According to the method of the invention, fluorescence from the analyte molecules immobilized on the solid phase can be counted as fluorescent spots by use of ordinary enlarging means. Examples of the enlarging means are a fluorescence microscope, and a scanning fluorescence microscope.

From measurement data (image) as a collection of the resulting fluorescent spots, analyte molecules can be detected visually or by a suitable detector with high sensitivity. For high sensitivity detection, I-CCD, SIT, PMT or SPD, for example, can be used preferably.

The analyte molecules labeled with the labeling material for highly sensitive fluorescence detection of the invention have been shown to be stained with a sufficient number of fluorochromes, and thus can be detected under an ordinary fluorescence microscope. Actually, the nucleic acid of more than 1,000 bases long of the invention can be intercalated with about 250 fluorochromes. The stained probe can then be detected as a spotty or linear fluorescent image under an ordinary fluorescence microscope. That is, the analytes labeled with the probe of the invention are detectable molecule by molecule as spots. By counting these spots, the labeled analyte molecules can be detected individually with ultrahigh sensitivity.

The type of fluorescence microscope devices used in the high sensitivity fluorescence detection method of the invention is not limited. The device with an ordinary objective lense of 20× to 100× magnification is preferably used. Concretely, the device may be one having a magnification of about 40× and possessing an image processor for counting of spots.

Data obtained based on the fluorescent spots can be processed by a zero-dimensional fluorescence intensity analysis system or an image analysis system (particle counting) in accordance with various purposes. Concretely, the background is measured to find the degree of nonspecific adsorption as the number of spots based on nonspecifically adsorbed labeling materials. The number of these background spots is statistically processed, whereby the significance of fluorescent spot counting data from the actual labeled analytes can be determined.

Figure 2:
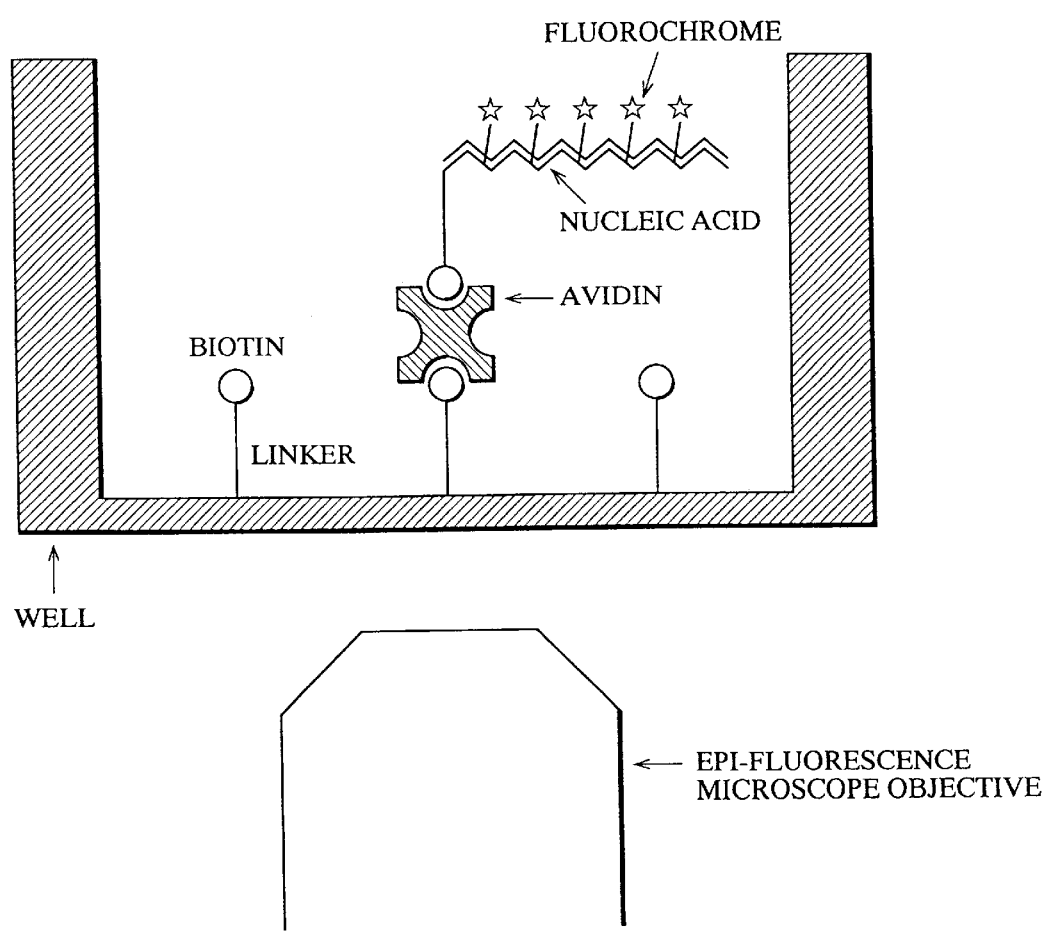
FIG. 2 is a drawing showing the method of observing a fluorescent-stained labeling nucleic acid, in which the inner surface of a microtiter plate is observed from below with an inverted epi-fluorescence microscope.
Figure 3:
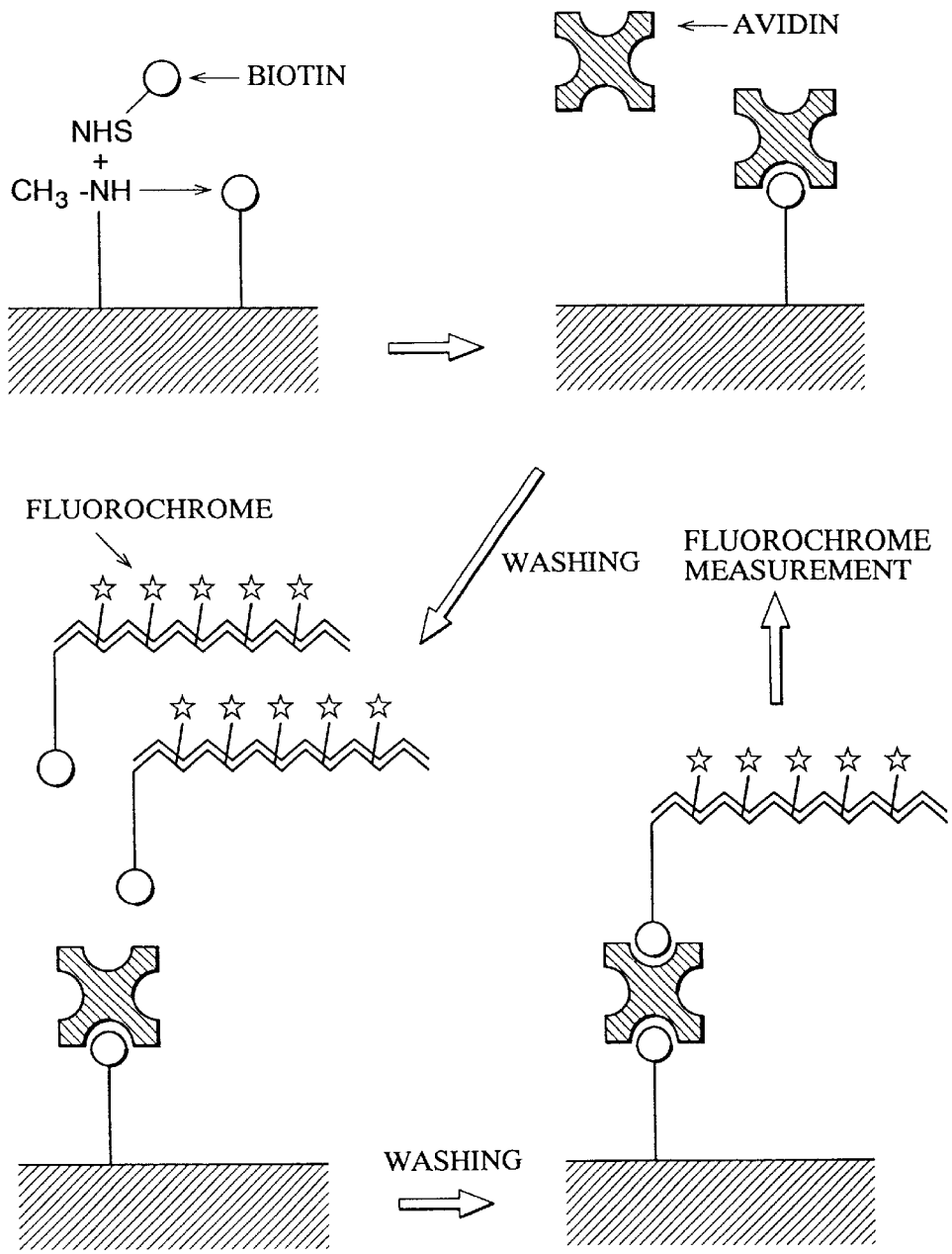
FIG. 3 shows an embodiment of the method related to the invention, illustrating the procedure of covalent bonding of biotin molecules to the surface of a solid phase, followed by washing, immobilizing avidin on biotin on the surface of the solid phase, followed by washing, further immobilizing a stained nucleic acid on the avidin, followed by washing, and measuring the labeled fluorescence.

FIGS. 2 and 3 show a preferred embodiment of the high sensitivity fluorescence detection according to the invention. As illustrated, a specific binding group (indicated here as biotin) is immobilized on a suitable solid phase (a well of a microtiter plate is schematically shown here) via a linker. On the so treated solid phase the high sensitivity fluorescence detecting, labeling material of the invention (a double-stranded nucleic acid is shown here) can be bound to an analyte (avidin in this case is shown here) via the specific binding group. This analyte-bound labeling material is then fluorometrically measured (or molecules with relevant fluorescent spots are counted) with a fluorescence microscope of a suitable magnification (the use of an epi-fluorescence microscope is schematically shown here) to find fluorescent spots in a predetermined area.

Figure 4:
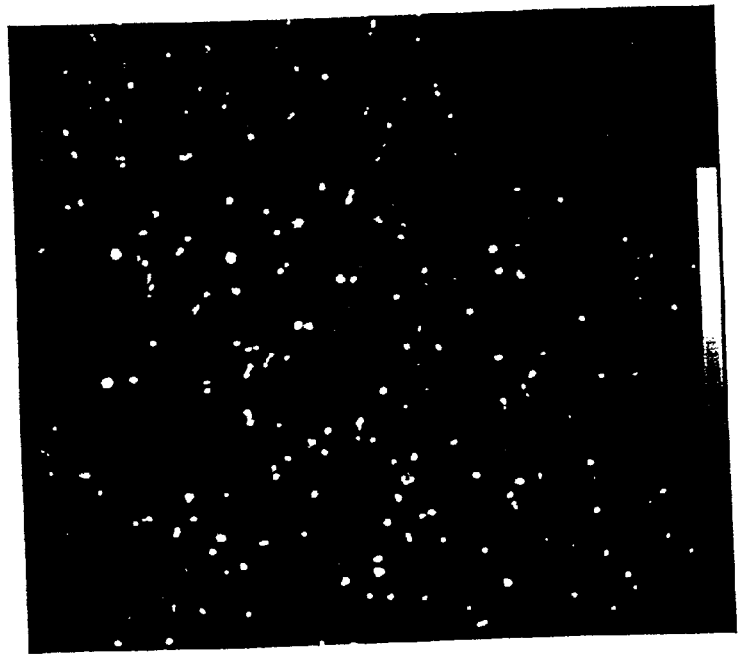
FIG. 4 is a fluorescence microscopic image of fluorescently stained nucleic acid molecules (lambda phage; length 48.5 kbp, 16 μm).

FIG. 4 shows, as a typical example, fluorescent spots from the labeled analyte immobilized on a slide glass. As demonstrated in FIG. 4, the number of fluorescent spots in a fixed area can be counted even visually at a suitable concentration. A more precise counting can be done by image processing of the resulting fluorescent spots. Concretely, background correction, correction of overlaps of the respective spots (based on the resolving power, magnification, etc. of the fluorescence microscope) and so on are performed on the basis of data on the locations and intensities of the respective spots. The background correction can be made by statistically processing (e.g., averaging) the fluorescence intensities from the parts other than the spots, and expressing the results as background fluorescence intensity or spot count. More than two spots measured can be evaluated as two spots. The overlapping spots can also be separated from each other by suitable image processing for purposes of correction.

Based on the aforementioed fluorescent spot counting, the number of the fluorescent spots is determined. From the number found, the number of molecules of the labeling materials or their concentration based thereon can be determined. Furthermore, the absolute number of molecules of the analyte, as well as the initial concentration of the analyte based on its value, can be determined. Concretely, a standard curve is depicted from the known concentrations of the analyte and the number of spots determined by measuring predetermined dilutions of the analyte labeled with the high sensitivity fluorescence detecting, labeling material of the invention. Based on this standard curve, it is possible to evaluate the presence of an unknown analyte or determine the concentration of the analyte.

The present invention will be described in more detail on the basis of the following Examples. However, the invention is in no way limited to these Examples.

EXAMPLE 1

DNA of lambda phage (length 48.5 kbp, 16 $\mu$m), PCR product of plasmid (length 4 kbp), and PCR product of plasmid (length 1 kbp) were fluorescently stained by simple mixing with YOYO-1 (Molecular Probe). The stained substances were each diluted and suspended in a 50% glycerin solution(v/v water). The suspension was sealed between a non-fluorescent slide glass and a cover glass, and observed from the cover glass side by use of a fluorescence microscope (AXIOBART, equiped with a 40× objective and a B-exciting dichroic mirror unit device, Zeiss).

As shown in FIG. 4, the stained substances can be easily observed, separately from each other, in a concentration-dependent manner as spotty or linear fluorescent images.

EXAMPLE 2

Analytes immobilized on the surface of a solid phase were determined using a microtiter plate. In a similar way as in Example 1, analytes labeled with arbitrary antigens, arbitrary ligands or specific labels (biotin, dinitrophenol, etc.) can be used as a model analytes.

Biotin for use as a model analyte was immobilized on the surface of a stationary phase, and detected with avidin, a protein specifically binding to biotin (schematically shown in FIGS. 2 and 3).

Biotin is immobilized by using a commercially available microtiter plate (CovaLink, Nunc) to whose inner wall a linker having an amino acid is already fixed. To join biotin to the amino group of the linker, the amino group of the linker was reacted using N-hydroxysuccinimidobiotin (NHS-biotin), a biotinylating reagent. It is known that one molecule of avidin can bind four molecules of biotin. So the avidin molecule bound to biotin on the surface of the solid phase, therefore, can still bind biotinylated nucleic acid molecules.

The nucleic acid used as a labeling material was the PCR amplified product of part of the plasmid pBluescript II KS+.

A 100 bases long nucleic acid and a 500 bases long nucleic acid were prepared using a common unmodified primer (5'-ATACCGTCGACCTCGAGG-3': Seq.ID No.1) and a biotinylated primer for 100 bases (5'-biotinylated-TCACACACAGGAAACAGCTA-3': Seq.ID No.2) and a biotinylated primer for 500 base product (5'-biotinylated-CGTCGATTTTTGTGATGC-3': Seq.ID No.3), respectively. A 3,000 base-long nucleic acid was prepared by using a biotinylated primer (5'-TCGGTTGAATGTCGCCCTTTTGTCTTTAGC-3': Seq.ID No.4) and an unmodified primer (5'-GAACAAAGAAACCACCAGAAGGAGCGGAAT-3': Seq.ID No.7), which amplifies a segment on the plasmid (about 3,000 bases). The length of the PCR amplified nucleic acid was confirmed by agarose gel electrophoresis. The resulting biotinylated nucleic acid was stained by simply mixing it with YOYO-1, an intercalating fluorochrome.

The fluorescently labeled biotinylated nucleic acid specifically bound via avidin to the immobilized biotin on the surface of the solid phase was then washed to remove unreacted avidin and labeling nucleic acid. Then, each well of the microtiter plate filled with phosphate buffer was measured from below by means of an inverted epi-fluorescence microscope equipped with a TV image processor. The TV camera used was an SIT camera type. The microscope was equiped with a B-exciting dichroic mirror unit (450 nm to 490 nm excitation; FT510 nm; fluorescence filter 545 to 565 nm) and a 40X objective lense and was focused on the inner wall of the bottom surface of each well. In this set-up, fluorescence image was photographed by 2-second accumulation. The fluorescence intensity of a 100 $\mu$m×100 $\mu$m region near the center of the accumulated fluorescence image was measured. The fluorescence intensity of phosphate buffer only was used as control and subtracted.

The resulting microscopic fluorescence varied depending on the concentration of NHS-biotin used when biotinylating the surface of the solid phase. The 3,000 base-long labeled nucleic acid molecules can also be identified as fluorescent spots when its concentration was not high.

Figure 5:
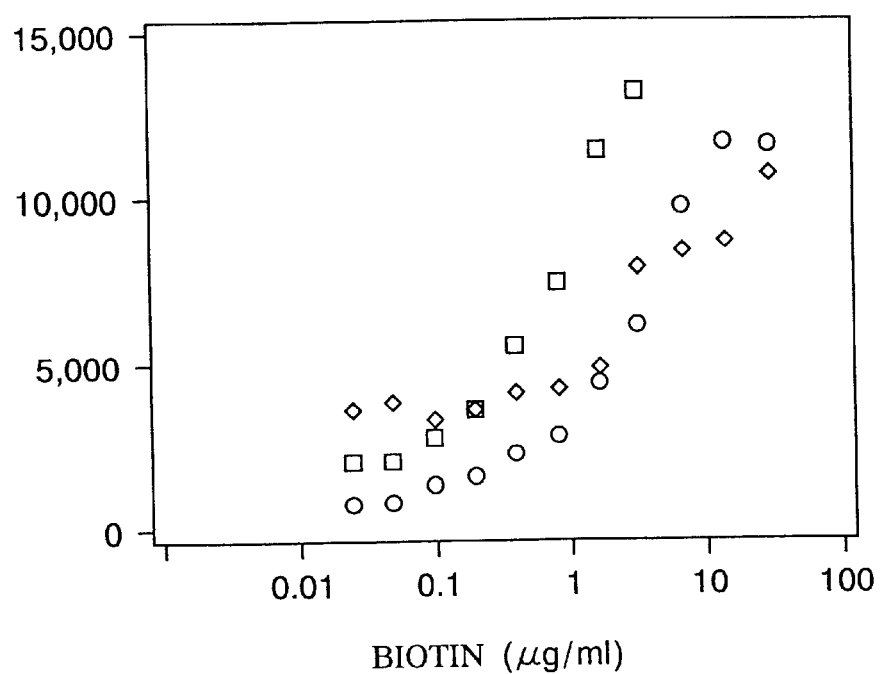
FIG. 5 shows changes in the total fluorescence intensity of a labeling nucleic acid in a measured area (100 μm×100 μm) as a function of the concentration of NHS biotin immobilized (○ signifies 100 bases long, □ 500 bases long, and ◇ 3,000 bases long)

Total intensities of the resulting fluorescent spots were plotted against the concentration of NHS-biotin used for the biotinylation of the surface of the solid phase. The concentration of NHS-biotin could be diluted until the fluorescence intensity is ascribed to the nonspecific adsorption of avidin in a concentration-dependent manner (FIG. 5). For comparison, enzyme-linked assay was also performed in parallel experiments to detect the concentration of NHS-biotin. This comparative enzyme-linked method achieved a detection limit comparable with nucleic acid of about 100 base-long. Thus, the method of the invention has been found to show sensitivity at least comparable with that by the enzyme labeling method in terms of fluorescence intensity determination. Total fluorescence determination also allows the use of an apparatus such as an existing commercially available microplate reader.

In the same manner as in the method described above for NHS-biotin, the concentrations of and the amounts adsorbed by an antigen, an antibody, a receptor and a ligand can be measured. To label an antibody, for example, a biotinylated antibody can further be labeled with the aforementioned biotinylated fluorescent labeled nucleic acid via avidin. Alternatively, a labeling nucleic acid having a functional group introduced at the terminal may directly be bonded covalently to the functional group of a side chain of the antibody. To impart fluorescing properties to the labeling nucleic acid, they may be incorporated when the nucleic acid is replicated and amplified enzymatically by PCR using a fluorescent nucleotide.

EXAMPLE 3

Figure 6:
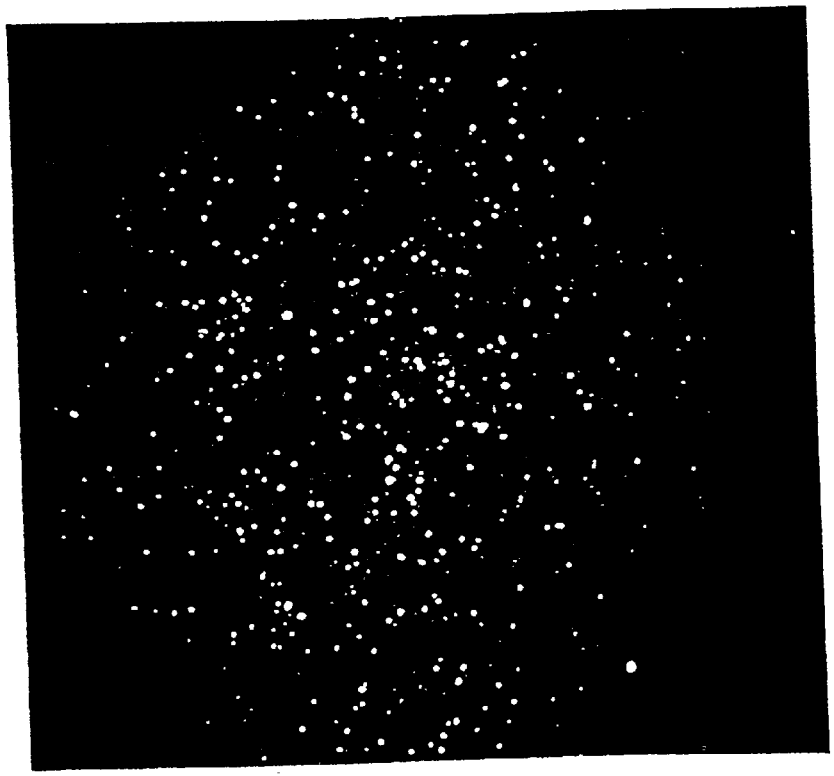
FIG. 6 is a fluorescence micrograph showing a part of PCR amplified lambda DNA using fluorochrome-labeled oligonucleotide.

As another method for introducing fluorescent labels into labeling nucleic acid, fluorochrome-labeled oligonucleotides were used as substrate to synthesize a labeling nucleic acid by PCR amplification. Furthermore, experiments were conducted in order to show that the nucleic acid molecules synthesized by this method could be individually observed with a fluorescence microscope. Fluorescein-dUTP (Fluorogreen, Amersham) was used as the fluorochrome-labeled oligonucleotide, and LA-PCR Kit (TAKARA) was used for synthesizing the labeling nucleic acid. The template for the labeling nucleic acid was lambda DNA. The primers were 5'-ATCATTATTTGATTTCAATTTTGTCCCACTCCC-3' (Seq.ID No.5) and 5'-AGGTCGCCGCCCCGTAACCTGTCGGATCACCGGA AA-3'(Seq.ID No.6). Using them, a part (20707 bp) of the lambda DNA was amplified. The amplified fluorescent labeled nucleic acid was separated from the excess fluorescein-dUTP by standard purification procedures. The separated nucleic acid was diluted and suspended in a 50% glycerol solution, and was observed with a fluorescence microscope in the same manner as in Example 1 (FIG. 6). This nucleic acid tended to be slightly lower in fluorescence intensity than the YOYO-1 stained nucleic acid, but the part of the lambda DNA (20707 bp) could be observed with the fluorescence microscope such that its molecules were individually observable.

EXAMPLE 4

Detection of Antigen-antibody Reaction.

Prostaglandin E2 conjugated with BSA (PGE2-BSA (bovine serum albumin)) immobilized on a slide glass by simple adsorption was reacted with anti-PGE2 antibodies. Then, avidin and YOYO-1 stained biotinylated lambda DNA were further linked, and the complex was observed with a fluorescence microscope.

The slide glass used was Silane coated slide (Sigma). Phosphate buffer (PBS) for dilution was adjusted to pH 7, and PBS for washing was adjusted to pH 7.5.

To adsorb PGE2-BSA on slide glass, 30 $\mu$l of a solution of the PGE2-BSA dissolved in PBS (pH 7) to each concentration (0.84 mg/ml, 0.164 mg/ml, 0 mg/ml) was placed on the slide glass. The solution on the slide glass was sealed with a cover glass and a rubber spacer, and incubated for 1.5 hours at room temperature, followed by washing with 300 $\mu$l of PBS three times. Then, to minimize the nonspecific absorption sites of the antibodies, 30 $\mu$l of a blocking buffer (BSA 1.68 mg/ml, PGE2-ELISA kit of Boehringer; catalog No. 1469231) was added, and incubated for 1 hour at room temperature. To couple with a nucleic acid, 30 $\mu$l of avidin (PGE2-ELISA kit of Boehringer) was further added, and incubated for 1.5 hours at room temperature, followed by washing 3 times. A fluorescent labeled nucleic acid was prepared by mixing 1 $\mu$l of 1 mM YOYO-1 with 80 $\mu$l of PCR product followed by dilution with demineralized water to 4 ml. The 30 $\mu$l of the fluorescent labeled nucleic acid solution was added to the solution of the(PEG2-BSA) on the slide glass, followed by incubation for 1 hour at room temperature and washing 3 times with 300 $\mu$l of PBS. Finally, more than 30 $\mu$l of PBS was added to remove air bubbles completely. Then, the system was sealed with a cover glass and a rubber spacer. The PCR amplification of the labeling nucleic acid was performed by 30 cycles of denaturation at 94° C. (20 seconds), annealing and extension reaction at 68° C. (15 minutes) using the following PCR mix:

| | |
|---|---|
| 10X PCR buffer (LA-PCR kit PRO13A, TAKARA) | 5 μl |
| Template (above kit) | 2 μl |
| Primer L1 (above kit) | 2 μl |
| Primer L2 (above kit) | 2 μl |
| Four dNTPs (above kit) | 8 μl |
| LATaq DNA polymerase (above kit) | 0.5 μl |

Figure 7A:
FIG. 7A is a fluorescence micrograph obtained when the concentration of added PGE2-BSA(30 μl) was 0.84 mg/ml.
Figure 7B:
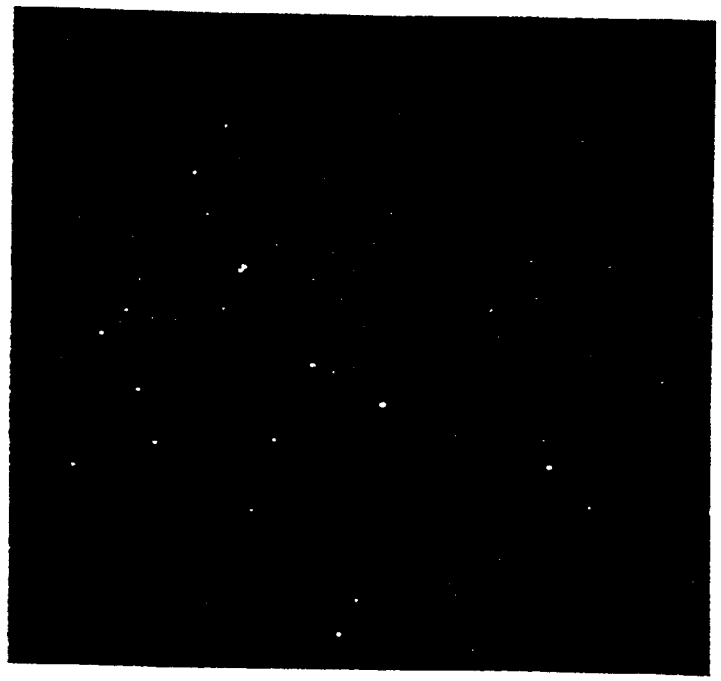
FIG. 7B is a fluorescence micrograph obtained when the concentration of added PGE2-BSA(30 μl) was 0.164 mg/ml.
Figure 7C:
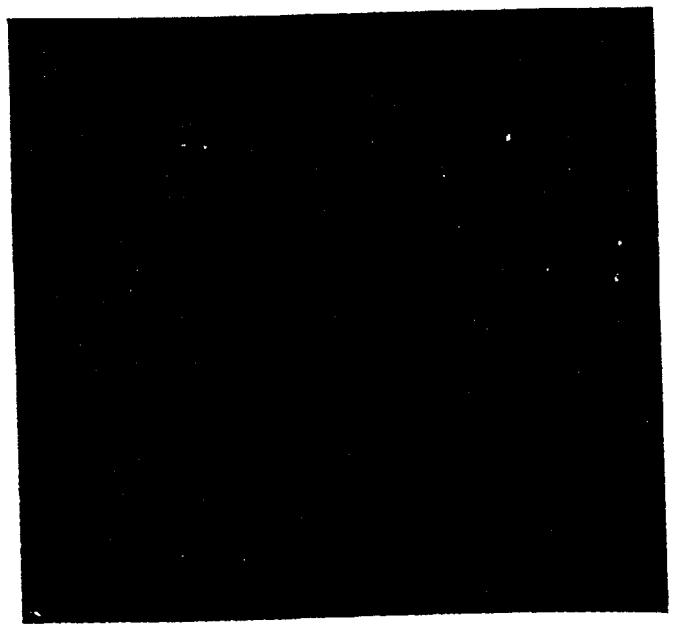
FIG. 7C is a fluorescence micrograph obtained when the concentration of added PGE2-BSA(30 μl was 0.0 mg/ml.

The resulting samples in solution were observed with a fluorescence microscope as in the experiments on the microtiter plate. The fluorescence microscope was Zeiss Axiovert135TV with objective 40× lense, equiped with an ARGUS50SIT camera system as a detector. Images of the YOYO-1 stained DNA bound to the antibodies are shown in FIGS. 7A to 7C. The concentrations of the PGE2-BSA adsorbed on the slide glass were 0.84 mg/ml, 0.164 mg/ml and 0.0 mg/ml, respectively, under the conditions in FIGS. 7A to 7C. Image processing by the ARGUS system was performed by particle counting to obtain the number of fluorescent spots corresponding to the concentration of the PGE2-BSA solution. The results showed a significant difference from that for the control at 0.0 mg/ml.

Figure 8:
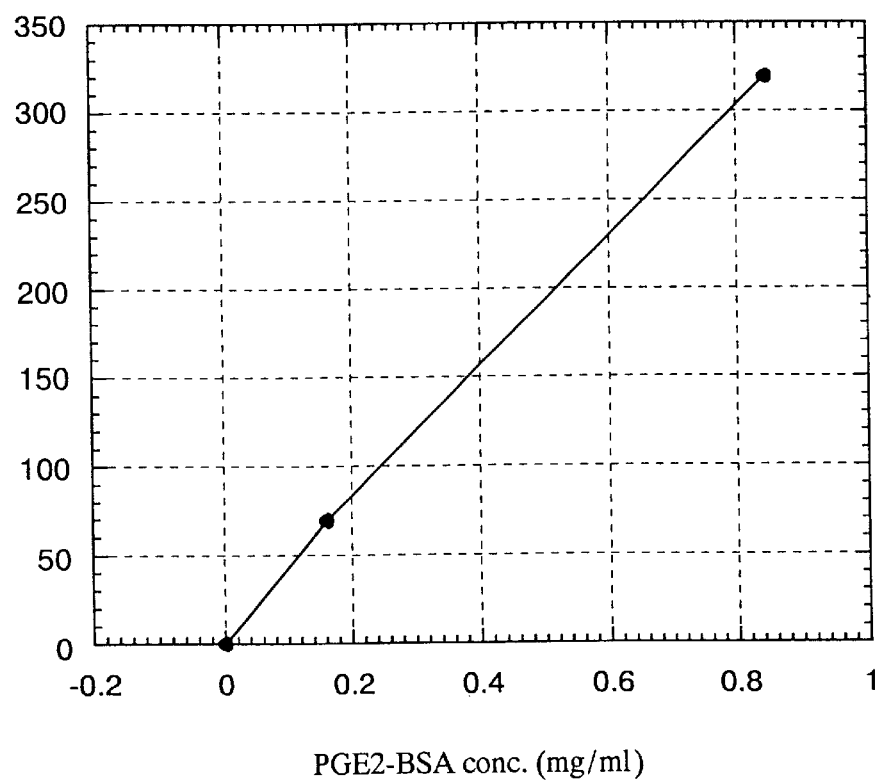
FIG. 8 shows the plot of the number of fluorescent spots, obtained by the image processing of FIGS. 7A to 7C, against the PGE2-BSA concentration.

FIG. 8 shows the plot of the number of the fluorescent spots obtained by image processing against the PGE2-BSA concentration. The plot showed a satisfactory linearity. In the instant Example, two spots were counted as nonspecific adsorptions. This result demonstrates that the use of the method of the invention enables the degree of nonspecific adsorption to be determined with high sensitivity.

Industrial Applicability

The high sensitive fluoroimmunoassay of the present invention relies on a labeling material having a nucleic acid stained with a sufficient number of fluorochromes, and further having a binding group for utilizing a specific binding reaction for labeling. Thus, substances labeled with this labeling material can be observed molecule by molecule with an ordinary fluorescence microscope. Moreover, very small amounts of biologically functional substances can be fluorescently detected rapidly and easily with high sensitivity. The method of the invention is as sensitive as, or more sensitive than, enzyme labeling methods. In addition, the use of a nucleic acid as a label gives higher stability and better storage than the use of an enzyme. Unlike enzyme labeling method, the method of the present invention requires no enzymatic reaction for detection, and ensures rapid assay.

What is claimed is:

1. Fluoroassay comprising the steps of:
providing a labeling fluorescent material having as a portion thereof, a biotinylated nucleic acid stained with fluorochrome molecules;
providing an avidin compound selected from avidin or streptavidin;
allowing any biotinylated analyte to bind to the labeling fluorescent material through biotin-avidin compound binding reaction; and
measuring the fluorescence of the labeled fluorescent material by counting the number of fluorescent spots on a fluorescence microscope with an optically magnifying means.
wherein the biotinylated nucleic acid portion is a single- or double-stranded nucleic acid having 100 to 50,000 bases, and the fluorochrome molecules are of the intercalation type or of the covalent bonding type to effect the staining, with the proviso that the biotinylated nucleic acid portion is a double-stranded nucleic acid when the fluorochrome molecules are of the intercalation type, and further wherein the number of fluorochrome molecules is 10 to 25% of the number of the nucleic acid base when the fluorochrome molecules are of the intercalation type, and the number of fluorochrome molecules is 10 to 70% of the number of the nucleic acid base when the fluorochrome molecules are of the covalent bonding type.

2. The fluoroassay of claim 1, further including the step of immobilizing the labeled analyte on a solid phase.

3. The fluoroassay of claim 1, wherein the biotinylated nucleic acid portion is a double-stranded nucleic acid having 1,000 to 5,000 bases.

4. The fluoroassay of claim 1, wherein the magnification of said fluorescence microscope is equal to or less than 500×.

* * * * *